(12) United States Patent
Vogel et al.

(10) Patent No.: US 7,618,382 B2
(45) Date of Patent: Nov. 17, 2009

(54) THERAPEUTIC APPARATUS FOR TREATING ULCERS BY APPLYING POSITIVE AND/OR NEGATIVE PRESSURES

(75) Inventors: Richard C. Vogel, San Antonio, TX (US); David M. Tumey, San Antonio, TX (US); Susan P. Morris, San Antonio, TX (US); L. Tab Randolph, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 176 days.

(21) Appl. No.: 11/365,433

(22) Filed: Mar. 1, 2006

(65) Prior Publication Data

US 2006/0149171 A1     Jul. 6, 2006

Related U.S. Application Data

(60) Continuation of application No. 09/458,280, filed on Dec. 10, 1999, now Pat. No. 7,214,202, which is a division of application No. 08/903,026, filed on Jul. 30, 1997, now Pat. No. 6,135,116.

(60) Provisional application No. 60/053,902, filed on Jul. 28, 1997.

(51) Int. Cl.
*A61H 7/00*     (2006.01)

(52) U.S. Cl. ............... 601/7; 601/10; 601/152

(58) Field of Classification Search .......... 601/6, 601/7, 9, 10, 11, 12, 13, 14, 148–152; 128/DIG. 20; 604/313–316

See application file for complete search history.

(56) References Cited

U.S. PATENT DOCUMENTS 1,355,846 A     10/1920     Rannells (Continued)

FOREIGN PATENT DOCUMENTS

AT          201229          12/1958

(Continued)

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(Continued)

*Primary Examiner*—Danton DeMille (57) ABSTRACT

A method and apparatus for providing concurrent applications of intermittent pneumatic compression therapy and vacuum assisted closure therapy generally comprises a wound dressing for introduction of a negative pressure into a wound on a patient's foot and a foot wrap for application of positive, compressive forces to substantially all of the patients foot. A suction pump, having an associated vacuum sensor and first feedback mechanism, supplies negative pressure to the wound dressing. A ventable source of pressurized gas, having an associated pressure transducer and second feedback mechanism, supplies positive force to the foot wrap. At least one control system is operably associated with the suction pump and ventable source of pressurized gas for controlling the negative and positive applications of pressure to the patient's foot. Controlled modes for operation include continuous or intermittent application of one or both therapies and simultaneous or cycled application of the therapies.

20 Claims, 7 Drawing Sheets

U.S. PATENT DOCUMENTS

| | | | |
|---|---|---|---|
| 2,098,272 A * | 11/1937 | Benson ............... | 601/6 |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,026,874 A | 3/1962 | Stevens | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,614,179 A | 9/1986 | Gardner et al. | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,007,411 A | 4/1991 | Dye | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,222,478 A | 6/1993 | Scarberry et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,443,440 A | 8/1995 | Tumey et al. | |
| 5,489,259 A | 2/1996 | Jacobs et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,701,917 A | 12/1997 | Khouri | |
| 5,840,049 A | 11/1998 | Tumey et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |

FOREIGN PATENT DOCUMENTS

| | | |
|---|---|---|
| AU | 550575 A1 | 8/1982 |
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| FR | 638 309 | 5/1928 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |

| | | |
|---|---|---|
| WO | WO 99/13793 | 3/1999 |

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp.: 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu, A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp.: 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

U.S. Appl. No. 08/517,901, filed Aug. 22, 1995, pp. 1-37.

KCI® The Clinical Advantage The V.A.C.®, Assisting in Wound Healing, Apr. 1997, 7pp.

U.S. Appl. No. 08/039,574, filed Mar. 25, 1993, pp. 1-71.

Kinetic Concepts, Inc., The Plexipulse® All in 1 System, Date Unknown, 2pp.

Dillon, Richard S., M.D., Treatment of Resistant Venous Stasis Ulcers and Dermatitis with the End-Diastolic Pneumatic Compression Boot, Angiology—The Journal of Vascular Diseases vol. 37: pp. 47-56, Jan. 1986.

Herrmann, Louis G., M.D., et al., The Conservative Treatment of Arteriosclerotic Peripheral Vascular Disease, Annals of Surgery vol. 100: pp. 750-760, Jul.-Dec. 1934.

Landis, Eugene M., et al, The Clinical Value of Alternate Suction and Pressure in the Treatment of Advanced Peripheral Vascular Disease, American Journal of the Medical Sciences vol. 189: No. 3, pp. 305-325, Mar. 1935.

Landis, Eugene M., et al., The Effects of Alternate Suction and Pressure on Blood Flow to the Lower Extremities, Journal of Clinical Investigation vol. 12: pp. 925-961, 1933.

Murray, James, M.D., On the Local and General Influence on the Body, of Increased and Diminished Atmospheric Pressure, Lancet 1: pp. 909-917, 1835.

Selahaddin Rastgeldi, Pressure Treatment of Peripheral Vascular Diseases, Supplementum XXVII, Opuscula Medica, 1972, pp. 1-18.

Selahaddin Rastgeldi, Intermittent Pressure Treatment of Peripheral Vascular Diseases, Supplementum XXVII Opuscula Medica 1972, pp. 19-49.

Gaskell P., et al The Effect of a Mechanical Venous Pump on the Circulation of the Feet in the Presence of Arterial Obstruction, Surgery, Gynecolgy & Obstetrics, Apr. 1978, vol. 146, pp. 583-592.

Parrott, J.C.W., The Effect of a Mechanical Venous Pump on the Circulation in the Feet in the Presence of Arterial Obstruction, Oct. 1972, pp. 1-108.

N.A. Bagautdinov, "Variant of External Vacuum Aspiration in the Treatment of Purulent Diseases of Soft Tissues," *Current Problems in Modem Clinical Surgery: Interdepartmental Collection*, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

* cited by examiner

THERAPEUTIC APPARATUS FOR TREATING ULCERS BY APPLYING POSITIVE AND/OR NEGATIVE PRESSURES

CROSS-REFERENCE TO RELATED APPLICATION

This is a continuing application, under 35 U.S.C. § 120, of U.S. application Ser. No. 09/458,280, filed Dec. 10, 1999, now U.S. Pat. No. 7,214,202 which is a divisional application of U.S. application ser. No. 08/903,026, filed Jul, 30, 1997, now U.S Pat. No. 6,135,116 which claims the benefit of U.S. application Ser. No. 60/053,902, filed Jul. 28, 1997; the prior applications are herewith incorporated by reference in their entirety.

BACKGROUND OF THE INVENTION

1. Field of the Invention

The present invention relates to methods and apparatus for treating foot ulcers. More particularly, the invention relates to methods and apparatus for applying positive and/or negative pressures to treat foot ulcers such as diabetic ulcers, arterial ulcers, venous stasis ulcers, pressure ulcers, and the like.

2. Description of the Related Art

Foot ulcers can be devastating—they are difficult to heal and are potentially limb-threatening. One of the difficulties is that a patient will often lose sensation in the area of an ulcer and, as a result, the patient tends to abuse the ulcer without notice. Foot ulcers, in particular, are troublesome because they are out of the patient's sight, especially when located on or near the patient's heel. Unseen and unfelt, the patient does not realize that the foot ulcer is colliding into a wheelchair, bedpost or the like. Consequently, the onset of a foot ulcer may place the foot at a significant risk for progression toward sepsis, gangrene and, ultimately, amputation.

Current treatment options for foot ulcers are varied, but all tend to be costly and traumatic; greater efficacy is thus desired. One of the most common treatment options is debridement of necrotic tissue followed by an attempt to physically close the ulcer, typically with sutures, skin grafts or the like. Unfortunately, many patients do not respond quickly, or at all, to such traditional treatment and the patient's condition often worsens. The resulting economic and emotional costs to the patient, and the patient's family, are staggering.

On the positive side, there have long been techniques available for promoting healthy circulation of body fluids. The concept of applying positive and/or negative pressure to help affect circulation is ancient, and many have sought to apply this concept to the foot in the form of inflatable boots that squeeze the foot and/or leg. Some have applied alternating positive and negative pressures, in a cyclic fashion, to first force blood out of the foot with positive pressure and then draw blood back into the foot with negative pressure. Recent products offered by Applicant under the trade designation "PLEXIPULSE" have provided intermittent compression, for a variety of indications, through pneumatic force externally applied to the foot. Such products are used, for example, to help prevent venous stasis and to promote circulation or to help treat and assist healing of cutaneous ulceration.

Another approach, for treatment of wounds, is represented by Applicant's products recently made commercially available under the trade designations "V.A.C." or "VACUUM ASSISTED CLOSURE." The "V.A.C." products generally comprise the application of negative pressure directly to a wound site, either on a continuous or intermittent basis. Such therapy units direct negative pressure to the wound site through a disposable pad, which includes a wound dressing and associated tubing, filters and drainage receptacles. The dressing itself includes a porous foam dressing sized to fit within the wound, the tubing directs the negative pressure into the foam, and the combination is sealed into the wound with the use of an adhesive drape that overlaps the entire wound site as well as a margin of surrounding intact skin. This therapy is promising for treatment of pressure ulcers and chronic open wounds, including decubitus ulcers and diabetic ulcers.

Both of the above-described therapies are currently available as of the filing date of this present application; despite the availability of such progressive therapies, however, foot ulcers continue to present serious concerns for patients and caregivers. It is therefore a fundamental object of the present invention to advance upon the prior art by providing an improved method and apparatus for effecting intermittent pneumatic compression concurrently with vacuum assisted closure. Many additional problems, obstacles and challenges present in existing modalities for the treatment of foot ulcers will be evident to caregivers and others of experience and ordinary skill in the art.

SUMMARY OF THE INVENTION

In accordance with the foregoing objects, the present invention—an improved method and apparatus for providing concurrent applications of intermittent pneumatic compression and vacuum assisted closure—generally comprises a wound dressing for introduction of a negative pressure into a wound on a patient's foot and a foot wrap for application of positive, compressive forces to substantially all of the patients foot. A suction pump, having an associated vacuum sensor and first feedback mechanism, supplies negative pressure to the wound dressing. A ventable source of pressurized gas, having an associated pressure transducer and second feedback mechanism, supplies positive force to the foot wrap. At least one control system is operably associated with the suction pump and ventable source of pressurized gas for controlling the negative and positive applications of pressure to the patient's foot.

In preparation for operation, the wound dressing is preferably first applied to the patient's foot followed by application of the foot wrap. Each is then in turn operably connected to its respective pressure source. Specifically, for application of the wound dressing, a porous pad, having plastic tubing inserted therein for connection to the suction pump, is inserted at least partially into the wound on a patient's foot. The wound dressing, and margin of impact surrounding the wound, is then preferably covered with a wound drape. The foot wrap, having fluid connection hardware associated therewith, is then placed in operable position over the wound dressing. Finally, the pad's plastic tubing is placed in fluid communication with the suction pump and the foot wrap's connection hardware is placed in fluid communication with the ventable source of pressurized gas.

In operation, negative pressure to the wound dressing is monitored and adjusted as necessary, by an integrated control system, to achieve desired therapy. Similarly, the positive, compressive force delivered to substantially the entire foot through the foot wrap is monitored and adjusted as necessary, also by an integrated control system, to achieve the desired therapy. Also effected by the integrated control system, the application timing of each component therapy is adjustable to allow concurrent application of pneumatic compression therapy and vacuum assisted closure therapy. It is to be understood that such concurrent therapy may entail continuous or intermittent application of one or both therapies and may or may not involve simultaneous application of the therapies.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiments follows together with illustrative figures, wherein like reference numerals refer to like components, and wherein.

DESCRIPTION OF THE PREFERRED EMBODIMENTS

By this reference, the full disclosures of Applicant's U.S. patent application Ser. No. 08/039,574 filed Mar. 23, 1993 and U.S. patent application Ser. No. 08/517,901 filed Aug. 22, 1995, are each incorporated herein as though set forth in their respective entireties. Copies of each of these applications are submitted herewith, through an accompanying Information Disclosure Statement, for entry into this application's file wrapper.

Although those of ordinary skill in the art will readily recognize many alternative embodiments, especially in light of the illustrations provided herein, this detailed description is exemplary of the preferred embodiments of the present invention, the scope of which is limited only by the claims appended hereto.

Figure 1:
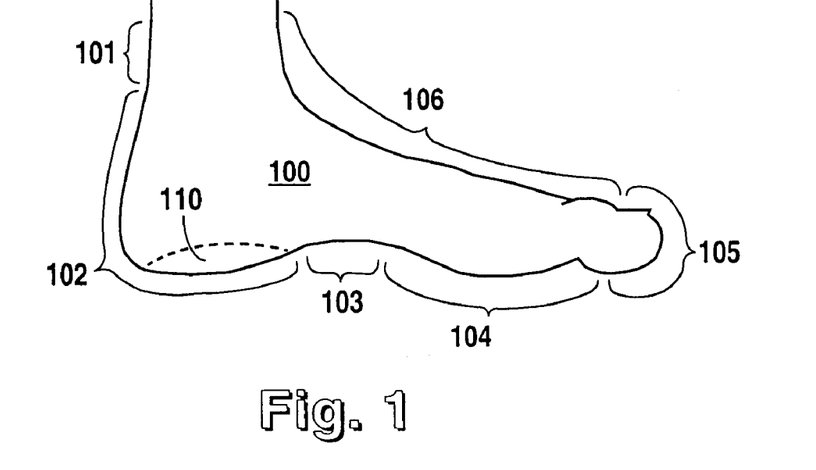
FIG. 1 illustrates, for reference purposes, regions 101-106 of a typical foot 100.

For reference purposes, various regions 101-106 of a typical foot 100 are shown in FIG. 1. Region 101 is referred to as the ankle region. Region 102 is referred to as the heel region. Region 103 is referred to as the plantar arch region. Region 104 is referred to as the metatarsal head, or ball, region. Region 105 is referred to as the toe region. Region 106 is referred to as part of the dorsal aspect region. Although these regions are shown as being mutually exclusive, this representation is for purposes of illustration only. It should be understood that one region may overlap another. For example, reference to the heel region 102 is not necessarily confined to that region illustrated in the drawings; the reference may actually include the heel region 102 and overlapping portions of adjacent regions such as the ankle region 101 or plantar arch region 103. The same may be true of references to the metatarsal head 104, or other, regions. Ulcers may occur either centrally or on either side of the foot 100 in any of the regions 101-106 shown; however, clinical evidence has shown that ulcers are most prevalent in the heel region 102 and the forefoot beneath the metatarsal head region 104. A representative location 1 10 of an ulcer is designated with a dashed margin in FIG. 1, at the bottom of the heel region 102.

Figure 8:
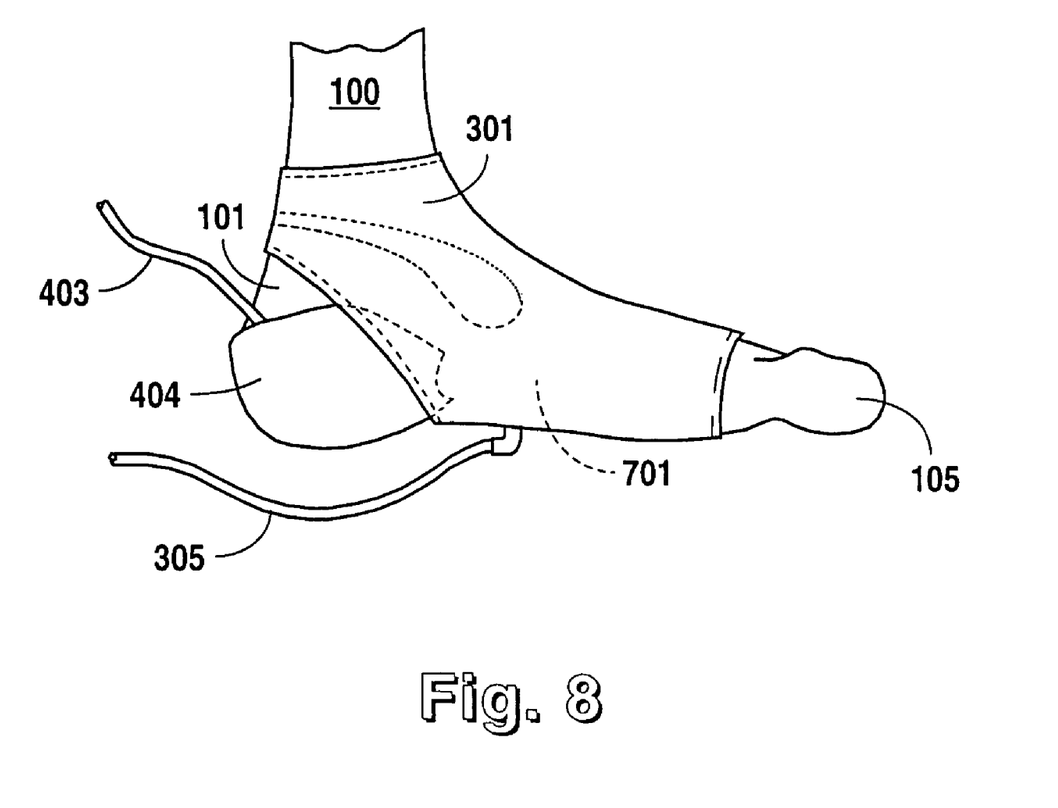
FIG. 8 shows a wound closure dressing 404 and foot compression wrap 301 as simultaneously applied to a human foot 100 in implementation of the preferred embodiment of the present invention.

FIG. 8 illustrates a typical preferred application of the present invention for treating and ulcer, or other wound, at ulcer location 110. Using the various apparatus and methods described further herein, localized negative pressure is induced on a foot 100 at the ulcer location 110 while positive, compressive force is applied to the foot 100. The resulting combination actively stimulates healing at the ulcer site 110 while also promoting healthy circulation of blood and nutrients.

Figure 2:
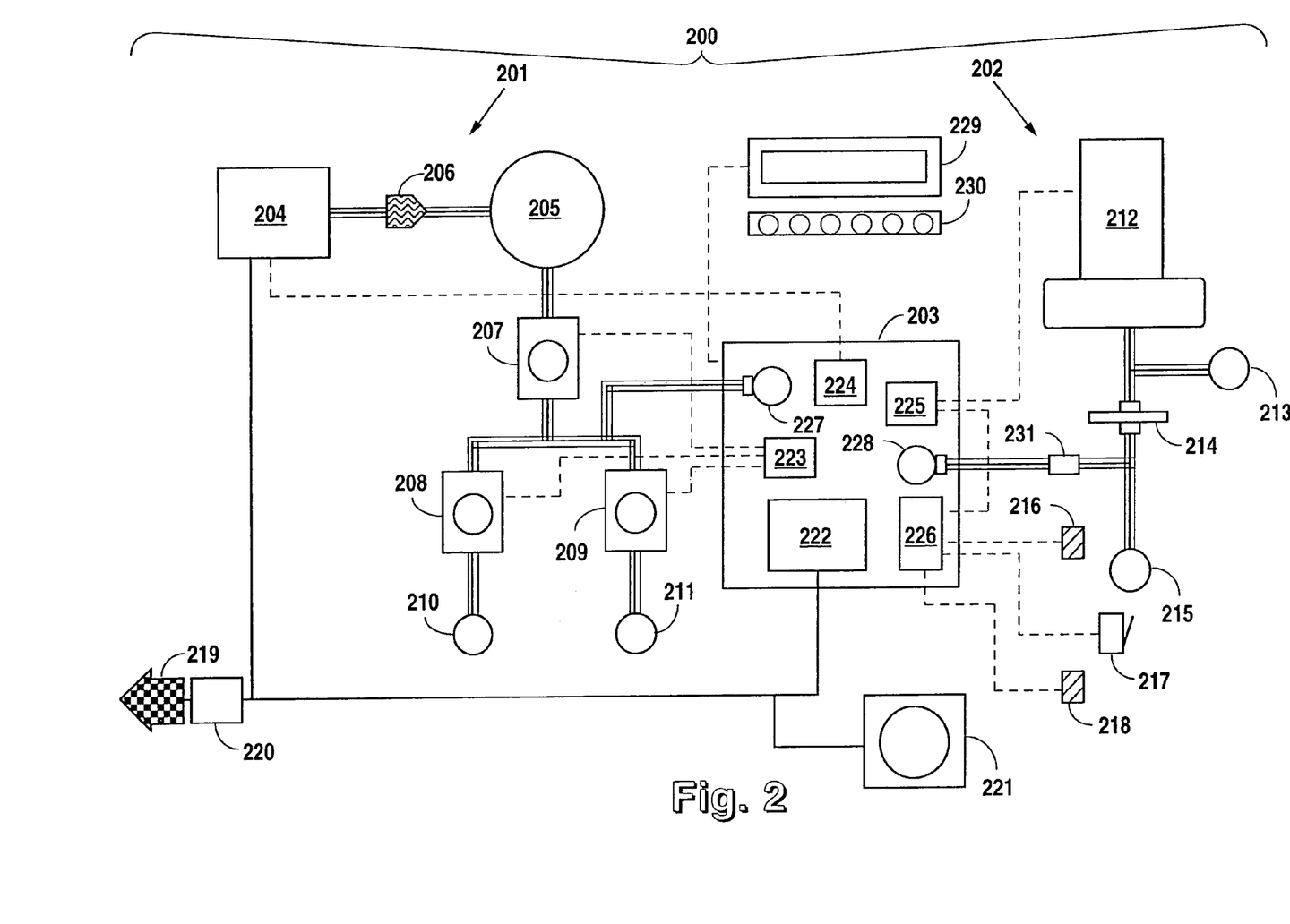
FIG. 2 shows, in a schematic block diagram, a first configuration 200 of the preferred embodiment of the present invention.
Figure 3:
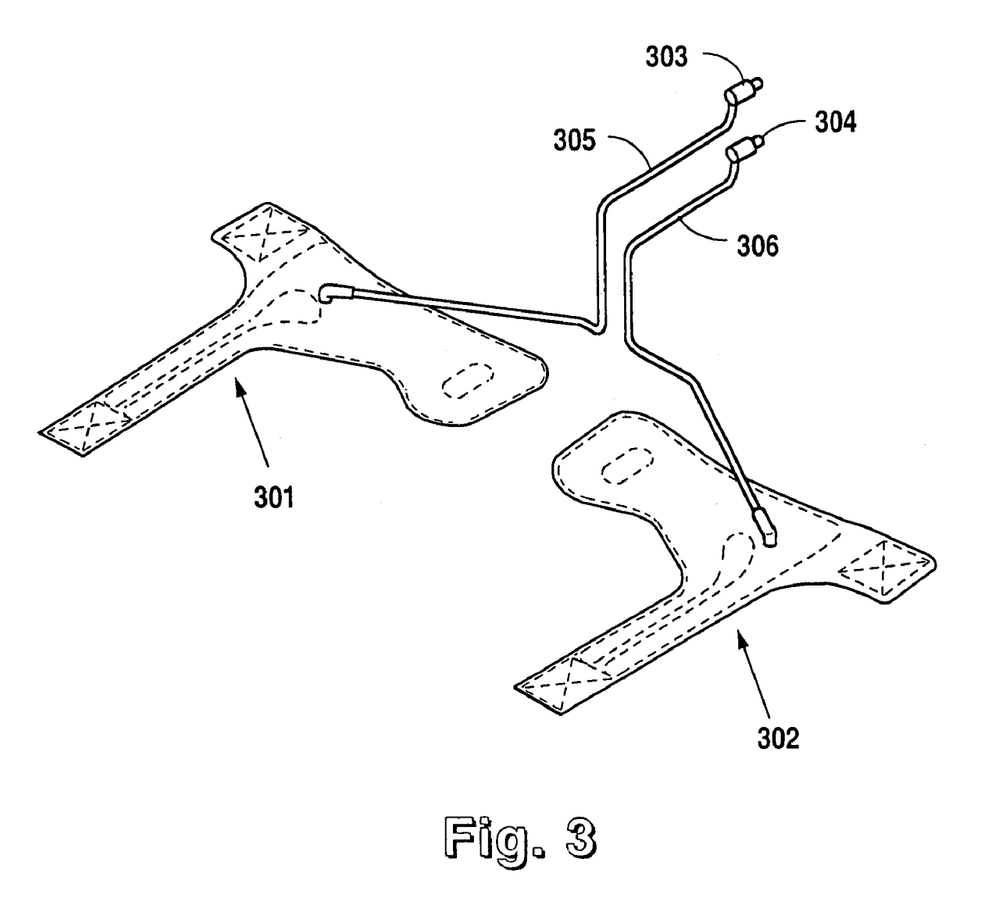
FIG. 3 shows, in perspective view, exemplary foot compression wraps 301, 302 as are utilized in the implementation of the preferred embodiment of the present invention.
Figure 4:
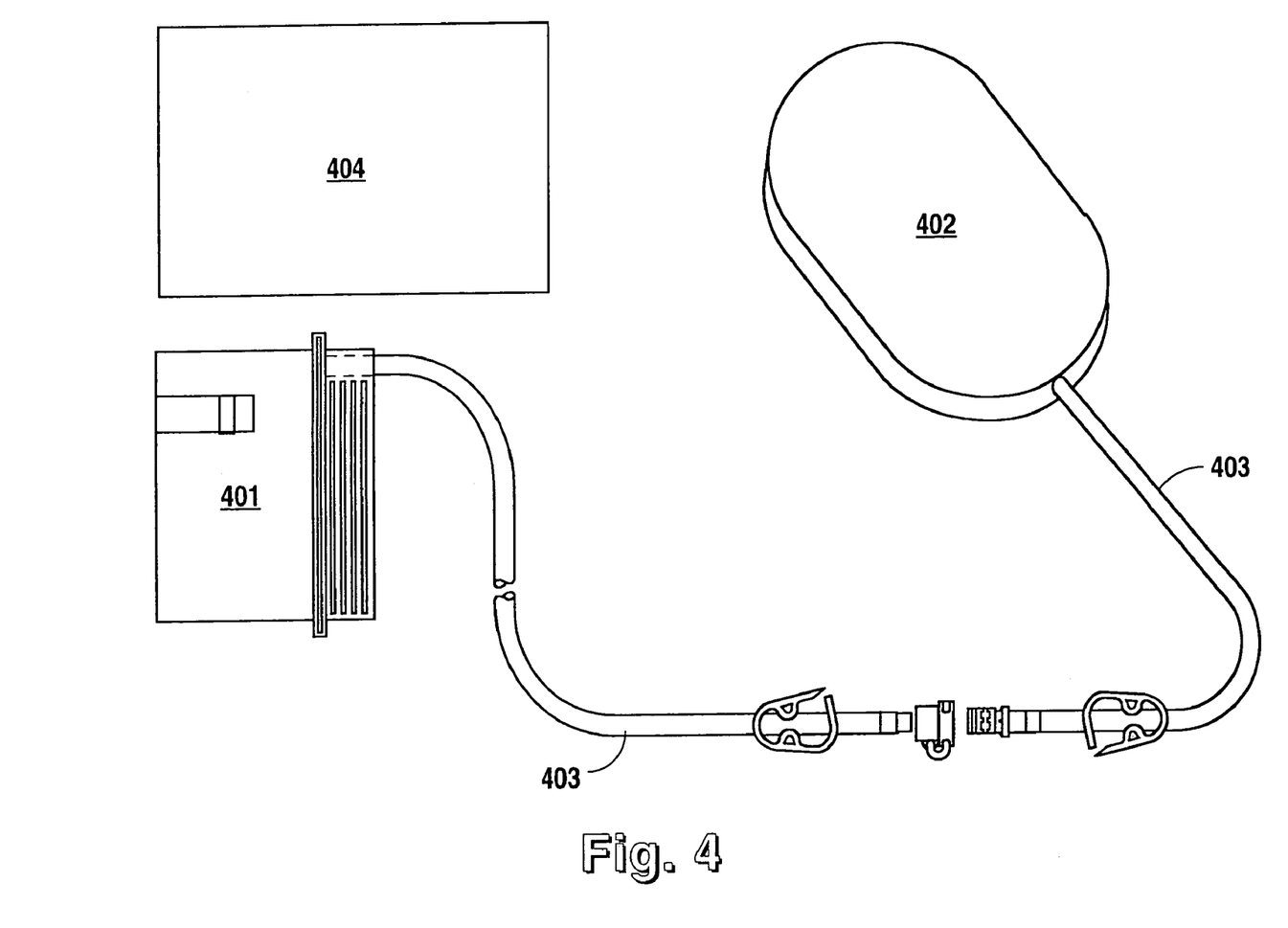
FIG. 4 shows, in semi-perspective view, an exemplary wound closure dressing 402 and fluid reservoir 401 as are utilized in the implementation of the preferred embodiment of the present invention.

Referring to FIGS. 2-4, there is shown a first configuration 200 of a system for therapeutic treatment of foot ulcers such as that shown at the ulcer location 110. This first configuration generally comprises an efficient combination of previously available vacuum assisted closure and intermittent pneumatic compression technologies for concurrent application of positive and negative pressures to an affected foot. According to the first configuration 200 of the preferred embodiment, there is generally provided an intermittent pneumatic compression unit 201 and a vacuum assisted closure unit 202 in operable communication with a single embedded micro-controller unit 203. The micro-controller unit 203 may be implemented in any of a variety of hardware and/or software designs as will be apparent to those of ordinary skill in the relevant arts. As will be apparent herein, the micro-controller unit 203 provides a single point of feedback driven control for both the intermittent pneumatic compression unit 201 and the vacuum assisted closure unit 202.

The intermittent pneumatic compression unit 201 of the first-configuration 200 generally comprises an oscillating air compressor 204 in fluid communication with an air reservoir 205 through a one-way check valve 206. As will be understood further herein, the check valve 206 serves to prevent pneumatic back flow from the air reservoir 205 to the oscillating air compressor 204 during periods in which the air compressor 204 is not in operation. The air reservoir 205 of the preferred embodiment is in fluid and operable communication with one or more foot compression wraps 301, 302 through a series of three-way solenoid valves 207-209, ports 210, 211, connectors 303, 304 and plastic, or other suitable material, tubing 305, 306.

Each of the solenoid valves 207-209 of the pneumatic compression unit 201 is chosen to be normally closed (when the coils are not energized) to the air reservoir 205 and normally open (when the coils are not energized) between the foot compression wraps 301, 302 and the atmosphere. When the coils are energized, atmosphere is closed off and a two-way pneumatic flow path is established between the air reservoir 205 and the foot compression wraps 301, 302. Two of the solenoid valves 208, 209 are designated as the left foot solenoid valve 208 and the right foot solenoid valve 209. Through this designation, independent control is maintained for inflation of either the left foot compression wrap 301, the right foot compression wrap 302, or both 301, 302. As will be further understood herein, the third solenoid valve 207 is necessary only in an alternate embodiment of the present invention and, even then, may be dispensed with in implementations utilizing solenoid valves 208, 209 having a "no-flow" capability.

The vacuum assisted closure unit 202 of the first configuration 200 of the preferred embodiment generally comprises a vacuum pump 212 in fluid communication with a fluid reservoir 401 through a dryer filter 214. An intake vent 213 is provided for connection, through appropriate tubing 403, of a porous foam dressing 402 to be inserted into a patient's wound 110, as will be understood further herein. The dryer filter 214 serves to protect the vacuum pump 212, which is not readily decontaminated, from the potentially hazardous or infectious wastes drawn from the wound site 110. A port 215 is provided for releasable connection to the fluid reservoir 401 in order that the reservoir 401 may be removed and discarded when full.

Various sensors are provided to promote safety in the operation of the system 200. For example, a mercury activated tilt sensor 216 indicates attitudes in which there is a danger of spilling fluids from the reservoir 401, a push-button interlock switch 217 in the back of the reservoir port indicates improper or incomplete placement of the reservoir 401, and a capacitively-activated level sensor 218 indicates a full condition of the reservoir 401. Feedback from any of these sensors 217-219 will cause termination of vacuum pump 212 operation, as will be understood herein. Those of ordinary skill in the art will quickly recognize that many other safety features may be integrated into the system 200 as desired.

Further details as to the construction and operation of the intermittent pneumatic compression unit 201, including the foot compression wraps 301, 302, may be gleaned from Applicant's U.S. patent application Ser. No. 08/039,574 filed Mar. 23, 1993 which has been incorporated herein by reference. Details as to the construction and operation of the vacuum assisted closure unit 202 may be gleaned from Applicant's U.S. patent application Ser. No. 08/517,901 filed Aug. 22, 1995 which also has been incorporated herein by reference. Those products embodying the foregoing applications, commercially available from Kinetic Concepts, Inc. of San Antonio, Tex. under the trade designations "PLEXIPULSE" and "V.A.C." are presently preferred by Applicant for implementation of this present invention. It is to be understood, however, that many other intermittent pneumatic compression and vacuum assisted closure products, as well as products for sequential therapy, wound drainage and other related therapies, are also presently available. Most all of these products should be considered functional equivalents for implementation of this present invention.

According to the preferred embodiment of the present invention, there is provided a single embedded micro-controller unit 203 for operation of both the intermittent pneumatic compression unit 201 and the vacuum assisted closure unit 202. The micro-controller unit 203, intermittent pneumatic compression unit 201 and vacuum assisted closure unit 202 all receive electrical power through a conventional wall plug 219 fitted with a hospital grade EMI/RFI filter, fuse and switch unit 220. A power supply 222 is provided with the micro-controller unit 203 for conversion of alternating current to direct current at an appropriate voltage level for the integrated circuitry and displays 229, 230 present on the unit 203. The micro-controller unit 203 is fitted with a conventional variable speed cooling fan 221, as is known in the art.

Additionally, the micro-controller unit 203 is provided with a solenoid valve control circuit 223, a compressor control circuit 224, a vacuum pump speed control circuit 225, a vacuum pump control circuit 226, a pressure sensor 227 and a vacuum sensor 228. Each circuit 223-226 of the unit 203 is operatively connected, directly or indirectly, to the system components being controlled and to the various sensors 227, 228 upon which operation of the system components is based. In operation, the solenoid valve control circuit 223 opens or closes the left and/or right solenoid valves 208, 209 according to a predetermined timing cycle in order to intermittently apply positive forces to substantially all, but in particular the plantar region 103, of the patient's foot 100.

In a preferred mode referred to as the "equilibrium mode," the oscillating air compressor 204 fills the air reservoir 205 to an automatically determinable target pressure, typically in the range of 350 mm Hg as measured by the pressure sensor 227. Once the pressure within the air reservoir 205 reaches the target pressure, the compressor 204 is shut off under the control of the compressor control circuit 224. Upon release of the compressed air into the left and/or right foot compression wraps 301, 302, an equilibrium pressure is reached between the air reservoir 205 and the wraps 301, 302. This equilibrium pressure, typically in the range of 160 mm Hg, is then measured by the pressure sensor 227 whereby an accurate indication of the actual pressure delivered to the plantar region arch 103 is obtained. The compressor control circuit 224 of the micro-controller unit 203 is then able to make use of this measurement to adjust, for subsequent compression cycles, the pressure of the air initially delivered to the air reservoir 205. Through this compression cycle-by-compression cycle adjustment scheme, the actual force applied to the patient's plantar region 103 may be robustly and accurately controlled, largely independent of wrap placement, changes in swelling or edema, or patient movements. Finally, at the end of the compression cycle and under the control of the solenoid valve control circuit 223, air is exhausted from the left and/or right foot compression wraps 301, 302, to the atmosphere, through the left and/or right solenoid valves 208, 209.

Alternatively, a third solenoid valve 207 may be incorporated to implement a timed-mode embodiment of the present invention. In this alternate embodiment, the oscillating air compressor 204 may operate continuously, the pressure ultimately delivered to the plantar regions 103 being controlled by the timed opening and closing of the third solenoid valve 207. According to the timed-mode embodiment, the air reservoir 205 is filled to the extent of the air compressor's capability, typically in the range of 800-900 mm Hg. Measurement of the initial pressure within the air reservoir is not necessary, so long as a relatively high pressure may be obtained within the capability of the air compressor 204. In operation, the solenoid valve control circuit 223 opens or closes the left and/or right solenoid valves 208, 209 in order to pre-select either the left or right foot, or both feet, for application of positive forces to the corresponding plantar regions 103. Substantially concurrent with the left and/or right foot selection, the solenoid valve control circuit 223 opens, for a short period of time, and then closes the third solenoid valve 207, causing a substantially impulsive burst of air to be released from the air reservoir 205 into the left and/or right foot compression wraps 301, 302. Following closure of the third solenoid valve 207, the pressure sensor 223 measures the pressure of the air released into the left and/or right foot compression wraps 301, 302. If necessary in order to achieve the desired compression wrap pressure, the open time of the third solenoid valve 207 may then be increased or decreased for subsequent compression cycles. Alternatively, the solenoid valve control circuit 223 may be implemented to produce only very short bursts of air from the air reservoir 205 into the foot compression wraps 301, 302. In this implementation, the number of bursts per compression cycle, and/or the time there between, may be increased or decreased during the present compression cycle, or in subsequent compression cycles, in response to the measured pressure in the foot compression wraps 301, 302. Like the equilibrium mode embodiment, the timed-mode embodiment provides a compression cycle-by-compression cycle adjustment scheme by which the actual force applied to the patient's plantar region 103 may be robustly and accurately controlled, largely independent of wrap placement, changes in swelling or edema, or patient movements. Finally, at the end of the compression cycle and under the control of the solenoid valve control circuit 223, air is exhausted from the left and/or right foot compression wraps 301, 302, to the atmosphere, through the left and/or right solenoid valves 208, 209.

In a further modification of the timed-mode embodiment, it is possible to dispense with the third solenoid valve 207 in favor of utilizing left and right solenoid valves 208, 209 having an intermediate "no-flow" capability. According to this modification, the left and right solenoid valves 208, 209 are normally closed (when the coils are not energized) between the foot compression wraps 301, 302 and the air reservoir 205 and the atmosphere, i.e. are in a "no-flow" state. Short bursts of air are then delivered from the air reservoir 205 to the left and/or right foot compression wraps 301, 302, according to the foregoing timed-mode methods, by toggling the left and/or right solenoid valves 208, 209 between their no-flow states and their states of open flow between the air reservoir 205 and respective wrap 301, 302. At the end of the compression cycle, air is exhausted from the wraps 301, 302 by opening the flow paths to the atmosphere. Although technologically feasible, such solenoid valves are not as of this date readily available; therefore, the three-valve implementation of the timed-mode embodiment is presently preferred over the two-valve implementation of the timed-mode embodiment.

In further operation, the negative pressure induced by the vacuum pump 212 is measured by a vacuum sensor 228 in fluid communication with the fluid reservoir 401 through an interposed orifice restrictor 231. The restrictor 231 serves to protect the vacuum sensor 228 from the relatively large negative pressures necessary in the treatment process as these pressures are typically too excessive for direct measurement under presently available sensor technologies. Vacuum feedback is monitored by the vacuum pump control circuits 226 to adjust the speed, through the vacuum pump speed control circuit 225, of the vacuum pump's motor in order to increase or decrease delivered vacuum. Additionally, the vacuum pump control circuit 226 monitors the various safety features 216-218 of the vacuum assisted closure unit 202 in order to effect shut down of the system 200 in the event of a hazardous condition.

Finally, all operations may be monitored through a liquid crystal display (LCD) readout 229 and/or light emitting diode (LED) display bar 230. Other feedback mechanisms, such as computer interfaces and others known to those of ordinary skill in the art, may be incorporated as desired. All such user interfaces are considered within the scope of the present invention.

Figure 5:
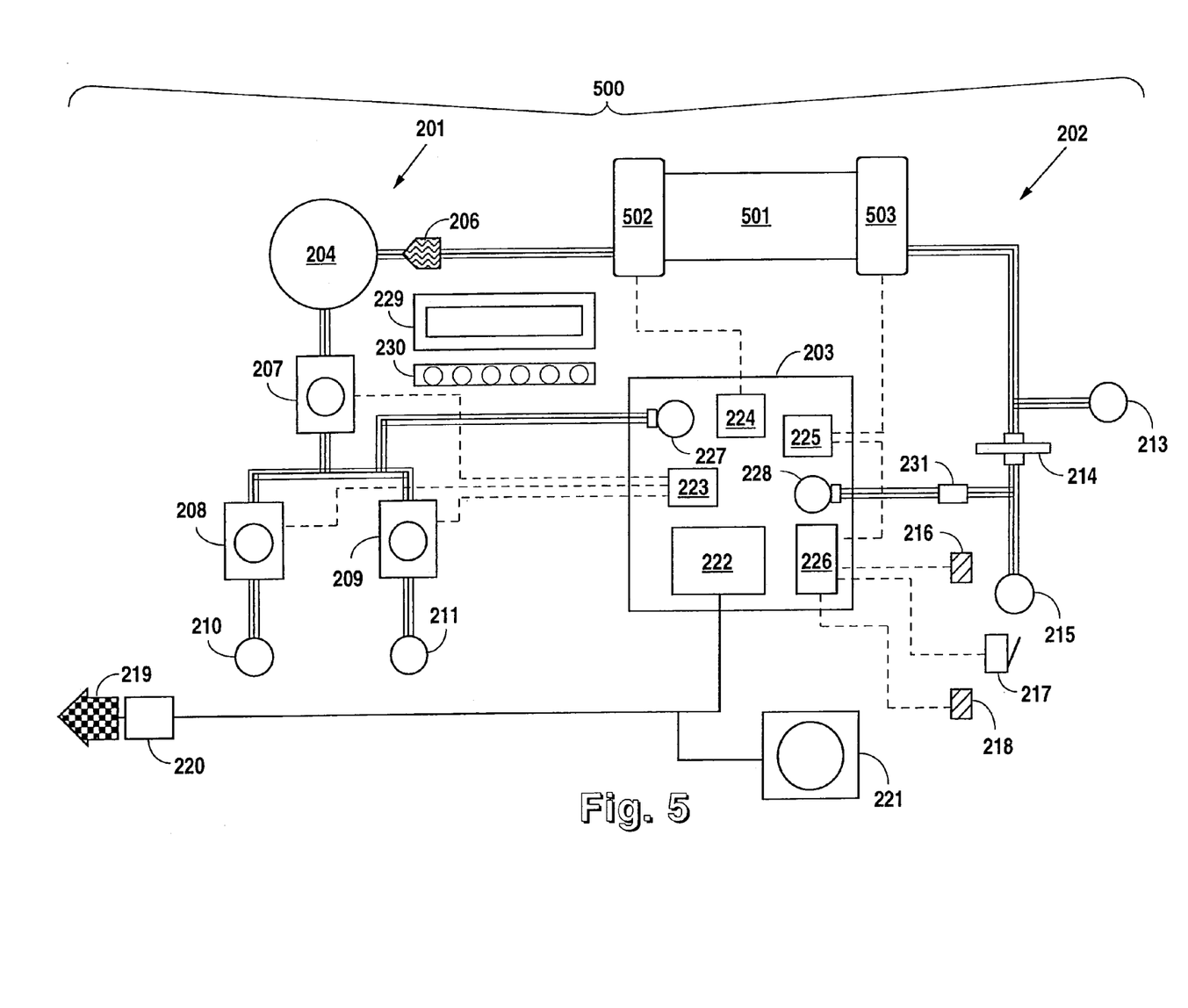
FIG. 5 shows, in a schematic block diagram, a second configuration 500 of the preferred embodiment of the present invention.

In a second configuration 500 of the preferred embodiment, shown in FIG. 5, the oscillating air compressor 204 and vacuum pump 212 are replaced by a single integrated compressor and vacuum pump unit 501 having internally thereto two separate plenums 502, 203. Operation is identical to that of the first configuration 200, with the exception that instead of speed control of the motors of the compressor 204 and vacuum pump 212, a clutch mechanism similar to that of automobile air conditioning units is utilized. Such mechanisms are readily understood by those of ordinary skill in the art. In essence, the appropriate control circuits 224, 225 generate pulse streams by which the respective clutch mechanisms are activated in pulse width modulated fashion.

Figure 6A:
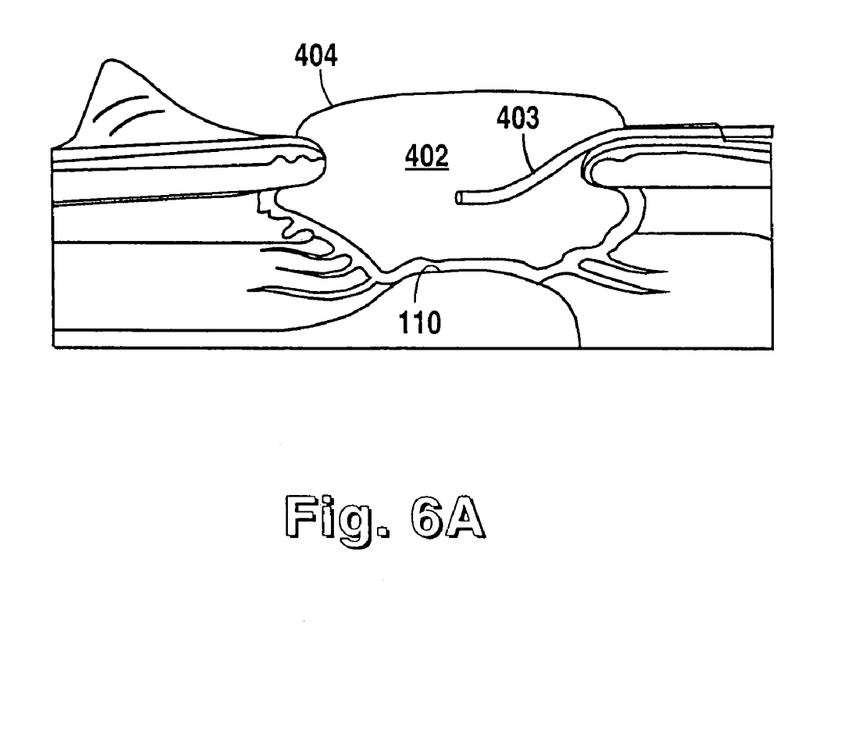
FIGS. 6A and 6B illustrate, in plan view, application, as taught for implementation of the preferred embodiment of the present invention, of a wound closure dressing 402, 404 to a human foot 100.
Figure 6B:
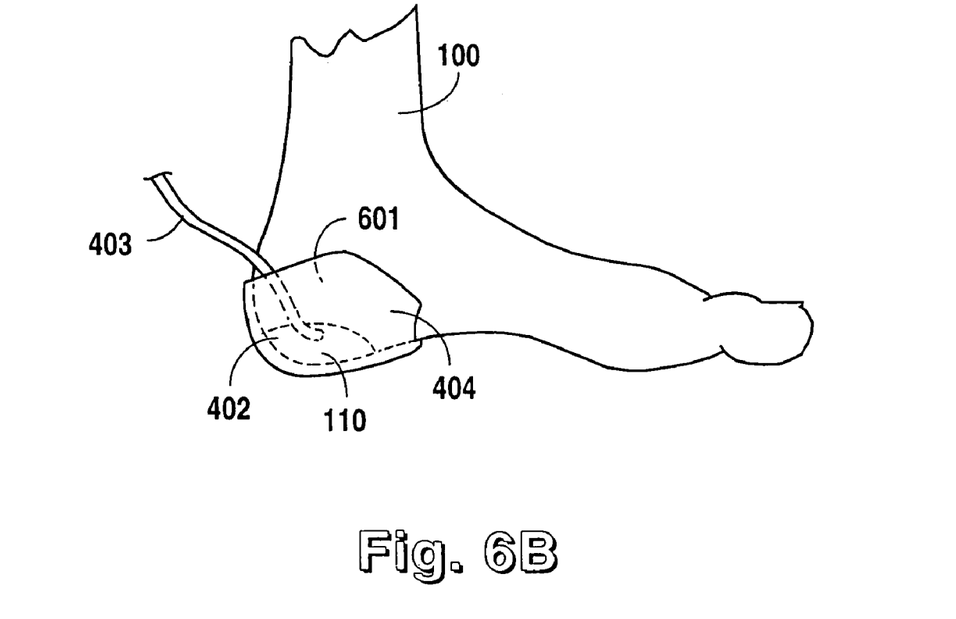

Referring to FIGS. 6A and 6B, there is shown the typical application of a wound closure dressing 402 to an example ulcer 110. Following debridement of necrotic tissue in and around the wound site 110, a porous foam dressing 402, having inserted therein tubing 403 for establishing fluid communication with the vacuum assisted closure unit 202, is inserted into the site 100. The porous foam dressing 402 and tubing 403 are anchored, and substantially sealed, within the wound site 110 by a covering of adhesive drape 404. The drape 404 physically covers the wound site 110 as well as the margin of impact 601 surrounding the wound site 110. A typical application, therefore, has a diameter of approximately four to eight inches, as measured if the drape 404 was laid flat.

In operation, the vacuum assisted closure unit 202 applies negative pressure, through the tubing 403, to the ulcer site 110. The porous foam dressing 402 serves to promote distribution of this negative pressure throughout the ulcer site 110. As a result, this distribution may be considered substantially uniform. The adhesive drape 404, itself or in concert with such other provisions as may be implemented by caregivers, serves to provide a seal around the wound site 110. This seal provides infection control for the wound while also minimizing leaks of the negative pressures applied thereto.

Figure 7A:
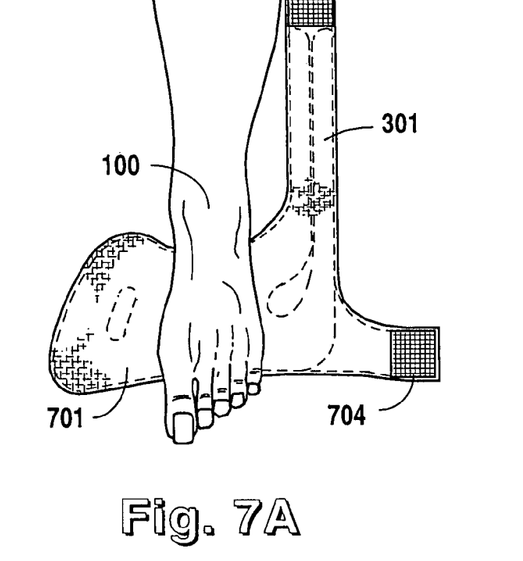
FIGS. 7A-7D illustrate, in perspective view, application, as taught for implementation of the preferred embodiment of the present invention, of a foot compression wrap 301, 302 to a human foot 100.
Figure 7B:
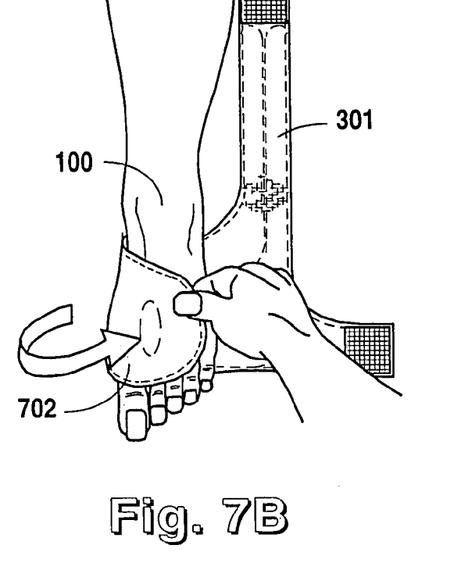
Figure 7C:
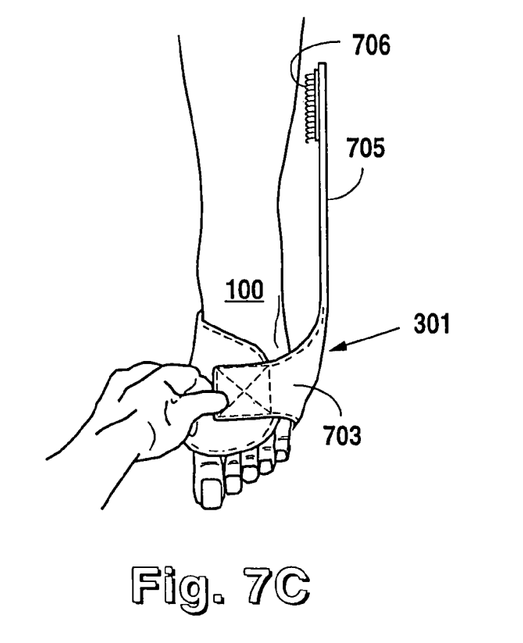
Figure 7D:
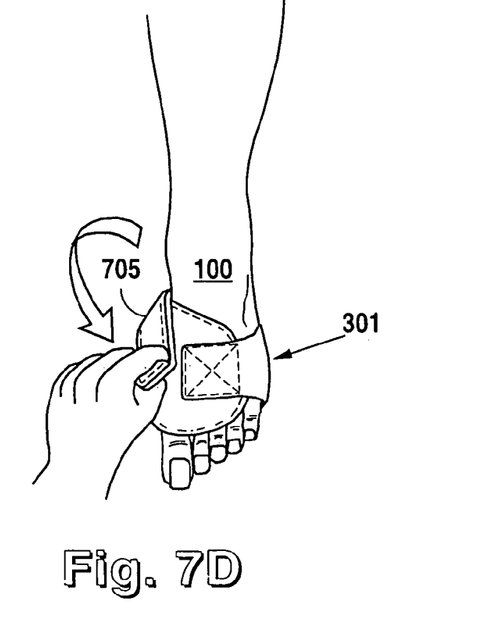

Referring now to FIGS. 7A-7D, there is shown the application of a foot compression wrap 301 to a foot 100. As shown particularly in FIG. 7A, the wrap 301 is first laid flat, generally beneath the heel, plantar arch and metatarsal head regions 102-104 of the foot 100. Then, as shown in FIG. 7B, a first tab 702 is wrapped about the dorsal aspect region 106 of the foot 100. A second tab 703, as shown in FIG. 7C, is next also wrapped about the dorsal aspect region 106 of the foot 100 and secured to the outside of the first tab 702 by conventional securing means such as, for example, releasably engageable hook and loop type material as is known by those of ordinary skill in the art and commercially available under the trademark "VELCRO." In the preferred embodiment of the present invention, a trademark "VELCRO" type patch 704 of hook-type material engages the outer surface of the wrap 301 which comprises hook compatible loop-type material. Finally, as shown in FIGS. 7C and 7D, a third tab 705 is wrapped about the ankle region 101 of the foot 100 and secured over the dorsal aspect region 106 by a tab 706 of hook-type material. As can be seen with reference to FIGS. 7A-7D, it is a specific object of such a foot compression wrap to cover a substantial portion of the foot with the inflatable bladder 701 integral thereto. In accordance with this object, both the deep and peripheral veins in the foot are compressed by operation of the intermittent pneumatic compression unit 201. This enables virtually complete emptying, on an intermittent basis, of the blood in the foot 100 to which the wrap 301, 302 is applied.

As clearly shown in FIG. 8, depicting the foot 100 with both the porous wound dressing 402, with drape 404, and the foot compression wrap 301 in operable position, portions of the heel region 102 and toe region 105 are not covered by the foot compression wrap 301 notwithstanding the object of compressing substantially the entire foot 100. This serves to enable viewing, by caregivers, of the exposed portions of the toe region 105 and heel region 102 for purposes of assessing the health of the foot 100 while the foot compression therapy is ongoing. This also readies skin on the foot 100 to minimize accumulation of moisture and the attendant risks of maceration.

In implementing the present invention, the wound closure dressing 402, 404 is applied first, in its entirety, and then the foot compression wrap 301 is applied. Due to the varying locations of ulcers on the foot 100, application of the foot compression wrap 301 may overlap the wound dressing site 601. Many applications within the scope of the present invention will also involve lapping the inflatable bladder 701 of the foot compression wrap 301 over the actual ulcer site 110. In such applications, the foam dressing 402 also serves the added function of helping to cushion the actual ulcer site 110 from the compressive action of the foot compression wrap 301. As shown in FIG. 8, the foot compression wrap 301 may overlap a portion of the ulcer site 110 to an extent that the inflatable bladder of the foot compression wrap 301 applies a compressive force over and onto the ulcer site 110.

Once the wound closure dressing 402 is operatively situated on an ulcer site 110 on the foot 100 of the patient and the foot compression wrap 301 or 302 is applied over the wound closure dressing 402 and its drape 404, the foot compression wrap 301 is then operatively connected to the intermittent pneumatic compression unit 201 and the wound dressing 402 is operatively connected to the vacuum assisted closure unit 202. Vacuum assisted closure therapy and intermittent pneumatic foot compression therapy can then be concurrently implemented, i.e., either simultaneously or in some indefinitely repeated cycle between positive and negative applications during which, it is to be understood, temporal overlap of positive and negative applications may or may not occur.

In the preferred embodiment of the present invention, the vacuum assisted closure unit 202 is provided with various settings for both intermittent and continuous application of negative pressure to the wound closure dressing 402. The most preferred selection of therapy options, i.e., intermittent or continuous vacuum, has not been determined at this time, although it is contemplated that either setting may be applicable. In any case, typical implementation of the invention will involve some periods of time during which negative pressure is actually applied to the ulcer site 110 notwithstanding the substantially concurrent application of compressive forces via the foot compression wrap 301, 302.

In a second mode of application of the present invention, the applications of positive and negative pressures are timed such that negative pressure is applied to the ulcer site 110 over a first period of time and positive pressure is then applied to substantially the entire foot 100 over a second period of time. Such alternating applications of negative pressure and positive pressure over the corresponding regions of the foot are then repeated indefinitely for the duration of the therapy.

While the foregoing description is exemplary of the preferred embodiments of the present invention, those of ordinary skill in the relevant arts will recognize the many variations, alterations, modifications, substitutions and the like as are readily possible, especially in light of this description, the accompanying drawings and claims drawn thereto. For example, while the preferred embodiment of the present invention calls for implementation of the intermittent pneumatic compression unit 201 and the vacuum assisted closure unit 202 in a single integrated unit 200, 500, those of ordinary skill in the art will recognize that, in the alternative, the present invention may be practiced, with only some corresponding loss in efficiency, with separate units for provision of intermittent compression therapy and vacuum assisted closure therapy. Such individual units are readily available and exemplary ones are described in detail in U.S. patent application Ser. No. 08/039,574 filed Mar. 23, 1993 and U.S. patent application Ser. No. 08/517,901 filed Aug. 22, 1995, each of which has been incorporated herein by reference. Products embodying each of these applications are commercially available from Kinetic Concepts, Inc. of San Antonio, Tex. under the trade designations "PLEXIPULSE" and "V.A.C." In such an alternate embodiment, calling for separate therapy units, synchronization of the therapy timing may be provided by interface circuitry, manual adjustment of the individual units or any number of other techniques readily available to those of ordinary skill in the relevant arts. Further, other modifications, such as the provision of independent, switched control of the intermittent pneumatic compression unit 201 and vacuum assisted closure unit 202 within the single integrated unit 200, 500, should be considered design expedients, within the scope of the present invention, especially in light of the foregoing exemplary description and appended claims. In any case, because the scope of the present invention is much broader than any particular embodiment, the foregoing detailed description should not be construed as a limitation of the scope of the present invention, which is limited only by the claims appended hereto.

We claim:

1. A therapeutic apparatus for treating ulcers, the apparatus comprising:
an intermittent pneumatic compression unit comprising an oscillating air compressor fluidly connected to an air reservoir through a one-way check valve;
a compression wrap fluidly connected to the air reservoir through a three-way valve;
a vacuum assisted closure unit comprising a vacuum pump fluidly connected to a porous foam dressing through an intake vent;
a single micro-controller unit comprising a three-way valve control circuit operably connected to the three-way valve, a compressor control circuit operably connected to the compression unit, a vacuum pump speed control circuit operably connected to the vacuum pump, a vacuum pump control circuit operably connected to the vacuum pump, a pressure sensor operably connected between the air reservoir and the compression wrap, and a vacuum sensor operably connected between the vacuum pump and the porous foam dressing;
whereby the micro-controller unit is operable to cause the compression unit to supply compressive force to the compression wrap and to cause the vacuum assisted closure unit to supply a vacuum to the porous foam dressing.

2. The apparatus of claim 1, wherein the micro-controller unit is programmed to supply compressive force to the compression wrap until reaching an equilibrium pressure between the compression unit and the compression wrap.

3. The apparatus of claim 1, wherein the compression wrap is adapted to be wrapped around a foot having a toe region and a heel region, without covering the toe region or the heel region.

4. The apparatus of claim 1, wherein the compression wrap has an inflatable bladder adapted to be placed over a region external to a wound.

5. The apparatus of claim 1, wherein the vacuum sensor measures pressure supplied to the porous foam dressing.

6. The apparatus of claim 1, wherein the porous foam dressing is adapted to be positioned adjacent a wound.

7. The apparatus of claim 6, further comprising a drape for covering said porous foam dressing.

8. The apparatus of claim 1, wherein the micro-controller unit provides a single point of feedback control of said vacuum assisted closure unit and said intermittent pneumatic compression unit.

9. The apparatus of claim 1, wherein the intermittent pneumatic compression unit applies the compressive force to the compression wrap intermittently.

10. The apparatus of claim 1, wherein the compression wrap comprises a plurality of compression wraps, and wherein each of the plurality of compression wraps is connected to the air reservoir.

11. The apparatus of claim 1, wherein the one-way check valve prevents pneumatic back flow from the air reservoir to the oscillating air compressor.

12. The apparatus of claim 1, wherein the three-way valve is a three-way solenoid valve.

13. The apparatus of claim 1, wherein the vacuum pump is in fluid communication with a fluid reservoir through a dryer filter.

14. The apparatus of claim 13, further comprising a capacitively-activated level sensor that indicates a full condition of the fluid reservoir.

15. The apparatus of claim 13, wherein the fluid reservoir is releasably connected to the vacuum pump via a port.

16. The apparatus of claim 13, wherein the vacuum sensor is in fluid communication with the fluid reservoir via an orifice restrictor.

17. The apparatus of claim 13, further comprising a push-button interlock switch that indicates incomplete placement of the fluid reservoir.

18. The apparatus of claim 1, further comprising a tilt sensor in communication with the micro-controller unit.

19. The apparatus of claim 1, wherein the three-way valve control circuit is a solenoid valve control circuit.

20. The apparatus of claim 1, wherein the oscillating air compressor and the vacuum pump are integrated into an integrated compressor and vacuum pump unit.

* * * * *